United States Patent
Ohyagi et al.

(10) Patent No.: US 11,815,433 B2
(45) Date of Patent: Nov. 14, 2023

(54) ADSORPTION APPARATUS AND CHEMILUMINESCENCE TYPE NITROGEN OXIDE CONCENTRATION METER

(71) Applicant: SHIMADZU CORPORATION, Kyoto (JP)

(72) Inventors: Norio Ohyagi, Kyoto (JP); Ryo Tanabe, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 228 days.

(21) Appl. No.: 16/402,474

(22) Filed: May 3, 2019

(65) Prior Publication Data

US 2020/0348277 A1 Nov. 5, 2020

(51) Int. Cl.
*G01N 21/76* (2006.01)
*B01D 53/04* (2006.01)
(Continued)

(52) U.S. Cl.
CPC ..... *G01N 33/0037* (2013.01); *B01D 53/0446* (2013.01); *B01D 53/261* (2013.01); *G01N 21/766* (2013.01); *G01N 2021/0193* (2013.01)

(58) Field of Classification Search
CPC . Y10T 436/177692; Y10T 436/178459; Y10T 436/179228; G01N 21/766;
(Continued)

(56) References Cited

U.S. PATENT DOCUMENTS 2,359,959 A * 10/1944 Anderson ............... F02B 19/12
123/169 PA
3,448,561 A * 6/1969 Seibert ............... B01D 53/0407
95/122
(Continued)

FOREIGN PATENT DOCUMENTS

JP 52-110281 A 9/1977
JP 54-75050 U 5/1979
(Continued)

OTHER PUBLICATIONS

Partial translation of JP 54-75050 U; p. 6, lines 6-12, USPTO Translations Service Center, (Year: 2023).*

(Continued)

*Primary Examiner* — Jennifer Wecker
*Assistant Examiner* — Michelle Adams
(74) *Attorney, Agent, or Firm* — Sughrue Mion, PLLC

(57) ABSTRACT

An inner diameter of an opening of the flow path is larger than a particle diameter of an adsorbent. Therefore, in a state where the flow path 33 is disposed in the container 31, the adsorbent 40 enters the flow path 33 via the opening 33B of the flow path 33. That is, in the adsorption apparatus, the adsorbent is disposed in a region between a side surface portion of the container and the flow path and inside the flow path. Further, in the adsorption apparatus 3, the air flows the region between the container 31 and the flow path 33 and in the flow path 33. Therefore, when the air is flown into the adsorption apparatus 3, the air can be sufficiently brought (Continued)

into contact with the adsorbent 40, and moisture contained in the air can be sufficiently adsorbed.

7 Claims, 3 Drawing Sheets

(51) Int. Cl.
  *G01N 33/00* (2006.01)
  *B01D 53/26* (2006.01)
  *G01N 21/01* (2006.01)
(58) Field of Classification Search
  CPC .............. G01N 33/0037; B01D 53/261; B01D 53/263; B65D 2517/0067; F24F 3/1411
  USPC ...................................... 49/40; 220/705–710
  See application file for complete search history.

(56) References Cited

U.S. PATENT DOCUMENTS

| | | | | |
|---|---|---|---|---|
| 4,394,144 A | * | 7/1983 | Aoki | B01D 53/261 |
| | | | | 206/204 |
| 4,541,851 A | * | 9/1985 | Bosquain | B01D 53/0438 |
| | | | | 96/126 |
| 5,089,035 A | * | 2/1992 | Kaneko | B01D 53/261 |
| | | | | 95/91 |
| 5,133,787 A | * | 7/1992 | Diot | B01D 53/0407 |
| | | | | 96/121 |
| 5,779,773 A | * | 7/1998 | Cam | B01J 8/008 |
| | | | | 55/494 |
| 2005/0115967 A1 | * | 6/2005 | Conaway | A47G 19/2266 |
| | | | | 220/254.1 |
| 2016/0158770 A1 | * | 6/2016 | Ransbarger | C10L 3/106 |
| | | | | 423/210 |

FOREIGN PATENT DOCUMENTS

| | | |
|---|---|---|
| JP | 2001-153857 A | 6/2001 |
| JP | 3108298 U | 4/2005 |
| JP | 2005-291656 A | 10/2005 |
| JP | 2018-069118 A | 5/2018 |
| JP | 2018072032 A * | 5/2018 |

OTHER PUBLICATIONS

Communication dated Oct. 29, 2019, from the Japanese Patent Office in counterpart Application No. 2016-208807.

* cited by examiner

ADSORPTION APPARATUS AND CHEMILUMINESCENCE TYPE NITROGEN OXIDE CONCENTRATION METER

CROSS REFERENCE TO RELATED APPLICATIONS

This application relates to, but does not claim priority from, JP Ser. No. JP2016-208807 filed on Oct. 25, 2016 and published as JP Pub. No. JP2018-69118 on May 10, 2018, the entire contents of which are incorporated herein fully by reference.

BACKGROUND OF THE INVENTION

Field of the Invention

The present invention relates to an adsorption apparatus storing an adsorbent therein, and a chemiluminescence type nitrogen oxide concentration meter equipped with the adsorption apparatus.

Description of the Related Art

Conventionally, an adsorption apparatus that adsorbs a component to be adsorbed contained in gas is utilized by an adsorbent stored therein. The adsorption apparatus is used, for example, by being interposed in the middle of a flow path through which gas passes. When gas flows into the adsorption apparatus, the gas moves in the internal space and comes into contact with the adsorbent, whereby the component to be adsorbed contained in the gas is adsorbed. Then, the gas after the component to be adsorbed is reduced is discharged from the adsorption apparatus.

As such an adsorption apparatus, for example, a dry air supply device that collects water vapor contained in the air by an adsorbent (desiccant) is utilized (for example, see Japanese Utility Model Registration No. 3108298).

In the dry air supply device described in Patent Document 1, an air passing pipe is disposed inside a desiccant storage container, and a region between the desiccant storage container and the air passing pipe is filled with a desiccant. A tip part of the air passing pipe is closed, and micro pores are formed on a circumferential surface thereof. Then, when air is flown into the desiccant storage container, water vapor contained in the air is collected by the desiccant, in the process that the air passes through the region between the desiccant storage container and the air passing pipe. Then, the air from which the water vapor has been removed flows into the air passing pipe from fine holes, and is discharged from the desiccant supply device via the air passing pipe.

As described above, in the dry air supply device described in Patent Document 1, water vapor contained in the air is removed with a simple configuration.

SUMMARY OF THE INVENTION

Problems to be Solved by the Invention

In the conventional dry air supply device described above, there was a problem that water vapor was not sufficiently removed. Specifically, in the conventional dry air supply device, the desiccant is filled only in the region between the desiccant storage container and the air passing pipe. Therefore, water vapor is removed by the desiccant only until the air flowing into the desiccant storage container reaches the vicinity of the air passing pipe. As a result, the desiccant cannot be sufficiently brought into contact with air, and there is a possibility that water vapor contained in the air cannot be sufficiently removed.

The present invention has been made in view of the above circumstances, and it is an object of the present invention to provide an adsorption apparatus capable of sufficiently adsorbing a component to be adsorbed by an adsorbent. Also, it is another object of the present invention to provide a chemiluminescence type nitrogen oxide concentration meter capable of accurately measuring the concentration of nitrogen oxides in a sample gas.

Means for Solving the Problems (1) The adsorption apparatus according to the present invention includes a container and a flow path. The container stores an adsorbent including particles. The flow path is inserted into the container and having an inner portion through which gas passes. The flow path located inside the container has a tip with an opening formed thereon. The opening having a size which is larger than a particle diameter of the adsorbent.

With such a configuration, in a state where the flow path is disposed inside the container, the adsorbent enters the flow path via the opening at the tip part of the flow path. That is, in the adsorption apparatus, the adsorbent is disposed in a region between the container and the flow path and inside the flow path. Further, in the adsorption apparatus, the gas flows between the container and the flow path, and inside the flow path.

Therefore, when the gas is flown into the adsorption apparatus, the gas can be sufficiently brought into contact with the adsorbent, and the component to be adsorbed contained in the gas can be sufficiently adsorbed.

(2) Also, a filling portion may be formed in the flow path. The filling portion is filled with an adsorbent in the container.

With such a configuration, the filling portion is filled with an adsorbent in the container which enters from the opening. Then, when the gas is flown into the adsorption apparatus, the gas can be sufficiently brought into contact with the adsorbent in the filling portion.

(3) In addition, the adsorption apparatus may further include a lid member. The lid member seals the container. The flow path may be attached to the lid member.

With such a configuration, an operation of inserting the flow path into the container and sealing the container with the lid member can be performed by a series of operations. Therefore, a user's operation can be simplified.

(4) Further, the lid member may be attached to and detached from the container by being rotated. The flow path may extend in a straight line along a rotation axis of the lid member.

With such a configuration, even when the lid member is rotated with respect to the container, the flow path can be arranged in a fixed position along the rotation axis.

Therefore, it is possible to prevent the flow path from hindering an attaching/detaching operation of the lid member.

As a result, the lid member can be smoothly attached to and detached from the container.

(5) Moreover, the flow path may have an end on an opposite side of the opening with a vent hole formed thereon.

With such a configuration, the gas flowing into the adsorption apparatus flows between the container and the flow path, then flows into the flow path via the opening, further flows inside the flow path, and then flows out from the flow path via the vent hole.

Therefore, the gas can be evenly flown in the adsorption apparatus.

As a result, the gas can be sufficiently brought into contact with the adsorbent, and the component to be adsorbed contained in the gas can be sufficiently adsorbed by the adsorbent.

(6) Furthermore, the adsorption apparatus may further include a filter. The filter is provided inside the flow path, and captures foreign matter in the gas passing through the flow path.

With such a configuration, when the gas is discharged from the flow path, foreign matter is captured by the filter in the process that the gas passes through the flow path.

Therefore, it is possible to prevent gas mixed with foreign matter from being discharged from the adsorption apparatus.

(7) A chemiluminescence type nitrogen oxide concentration meter according to the present invention includes the adsorption apparatus, an ozone generator, a reaction unit, a detector, and a measurement unit. The ozone generator generates ozone using air from which moisture has been adsorbed by the adsorption apparatus. The reaction unit causes chemiluminescence of nitrogen oxides in a sample gas using ozone generated in the ozone generator. The detector detects an intensity of light generated by chemiluminescence in the reaction unit. The measurement unit measures a concentration of nitrogen oxides in the sample gas, based on the intensity of light detected by the detector.

With such a configuration, it is possible to generate ozone satisfactorily in the ozone generator. Then, nitrogen oxides are made to show chemiluminescence using the ozone in the reaction unit, the intensity of light generated by chemiluminescence is detected in the detector, and the concentration of nitrogen oxides in the sample gas is measured in the measurement unit, based on the intensity of light detected by the detector.

Therefore, the concentration of nitrogen oxides in the sample gas can be accurately measured.

Effects of Invention

According to the present invention, in the adsorption apparatus, the adsorbent is disposed in the region between the container and the flow path and inside the flow path. Therefore, when the gas is flown into the adsorption apparatus, the gas can be sufficiently brought into contact with the adsorbent, and the component to be adsorbed contained in the gas can be sufficiently adsorbed.

MODE FOR CARRYING OUT THE INVENTION

Figure 1:
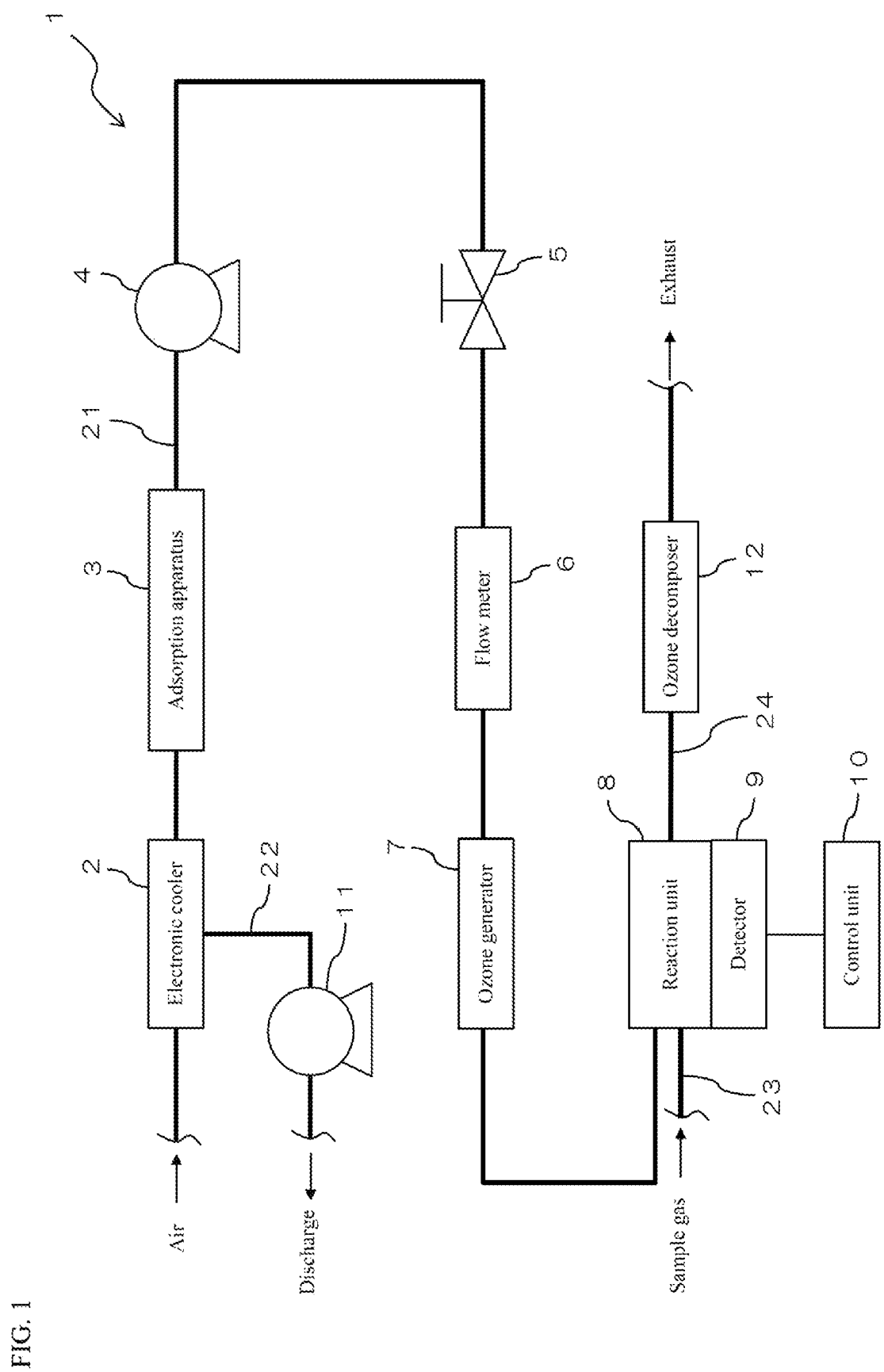
FIG. 1 is a schematic diagram showing a configuration of a chemiluminescence type nitrogen oxide concentration meter according to one embodiment of the present invention.

1. Overall Configuration of Chemiluminescence Type Nitrogen Oxide Concentration Meter FIG. 1 is a schematic diagram showing a configuration of a chemiluminescence type nitrogen oxide concentration meter 1 according to one embodiment of the present invention.

The chemiluminescence type nitrogen oxide concentration meter 1 is a device for measuring the concentration of nitrogen oxides contained in a sample gas. The chemiluminescence type nitrogen oxide concentration meter 1 includes an electronic cooler 2, an adsorption apparatus 3, a first pump 4, a valve 5, a flow meter 6, an ozone generator 7, a reaction unit 8, a detector 9, a control unit 10, a second pump 11, and an ozone decomposer 12. Further, in the chemiluminescence type nitrogen oxide concentration meter 1, a first flow path 21, a second flow path 22, a third flow path 23, and a fourth flow path 24 are formed.

The first flow path 21 is a flow path for taking in air and mixing ozone ($O_3$) into the air and flowing it into the reaction unit 8. In the first flow path 21, the electronic cooler 2, the adsorption apparatus 3, the first pump 4, the valve 5, the flow meter 6 and the ozone generator 7 are interposed in this order, and an end on a downstream side in the moving direction of the air is connected to the reaction unit 8.

The electronic cooler 2 is for adjusting the air flown into the first flow path 21 so that its temperature and humidity become respectively constant. To the electronic cooler 2, one end of the second flow path 22 is connected. In the second flow path 22, a second pump 11 is interposed. By operating the second pump 11, moisture removed from the air in the electronic cooler 2 is discharged via the second flow path 22.

The adsorption apparatus 3 is for further dehumidifying the air of which the temperature and the humidity have been adjusted by the electronic cooler 2. As will be described in detail later, the adsorption apparatus 3 adsorbs and removes moisture contained in the air to dehumidify the air.

The first pump 4 sucks air into the first flow path 21, causes the sucked air to pass through the first flow path 21, and sends the air to the reaction unit 8.

The valve 5 is for adjusting the flow rate of the air moving in the first flow path 21 to be constant. The valve 5 is, for example, a needle valve.

The flow meter 6 is for measuring the flow rate of the air moving in the first flow path 21.

The ozone generator 7 is an apparatus for generating ozone using the air moving in the first flow path 21. Specifically, the ozone generator 7 generates ozone by silent discharge or the like.

One end of the third flow path 23 is connected to the reaction unit 8. Air containing ozone is flown into the reaction unit 8 via the first flow path 21 and the sample gas is supplied to the reaction unit 8 via the third flow path 23. The reaction unit 8 causes chemiluminescence of nitrogen oxides contained in the sample gas, using ozone contained in the air.

The detector 9 is adjacent to the reaction unit 8. The detector 9 includes, for example, a glass window or the like, and is configured so that light generated by chemiluminescence in the reaction unit 8 can be taken in. The detector 9 is configured to detect the intensity of light generated in the reaction unit 8.

The control unit 10 includes, for example, a Central Processing Unit (CPU). The control unit 10 is electrically connected to the detector 9. The control unit 10 controls the operation of the detector 9 and measures the concentration of nitrogen oxides in the sample gas, based on the intensity of light detected by the detector 9. The control unit 10 is an example of the measurement unit.

One end of the fourth flow path 24 is connected to the reaction unit 8. In the fourth flow path 24, an ozone decomposer 12 is interposed.
The ozone decomposer 12 decomposes unreacted ozone contained in the air by thermal decomposition or the like.

In the chemiluminescence type nitrogen oxide concentration meter 1, the first pump 4 and the second pump 11 are operated, and the opening of the valve 5 is adjusted so that the flow rate detected by the flow meter 6 becomes constant. Then, a certain amount of air is sucked into the first flow path 21 and moves in the first flow path 21.

At this time, the air moving in the first flow path 21 is adjusted to a constant temperature and constant humidity by the electronic cooler 2, and then further dehumidified by the adsorption apparatus 3. The air that has been dehumidified by the adsorption apparatus 3 flows into the ozone generator 7. Then, ozone is generated in the ozone generator 7. Ozone generated in the ozone generator 7 flows into the reaction unit 8 together with the air. Further, a sample gas is supplied to the reaction unit 8 via the third flow path 23.

Then, in the reaction unit 8, the sample gas and ozone are chemically reacted to generate light. At this time, the detector 9 detects the intensity of the light generated in the reaction unit 8. The control unit 10 measures the concentration of nitrogen oxides in the sample gas, based on the detection result of the detector 9. Further, in air that has passed through the reaction unit 8, unreacted ozone is decomposed by the ozone decomposer 12 in the process of moving the fourth flow path 24, and then the air is exhausted.

As described above, in the chemiluminescence type nitrogen oxide concentration meter 1, the air dehumidified by the adsorption apparatus 3 is used to generate ozone, and a chemical reaction is performed in the reaction unit 8 using the ozone. The adsorption apparatus 3 is configured as follows so as to efficiently dehumidify air.

2. Detailed Configuration of Adsorption Apparatus

Figure 2:
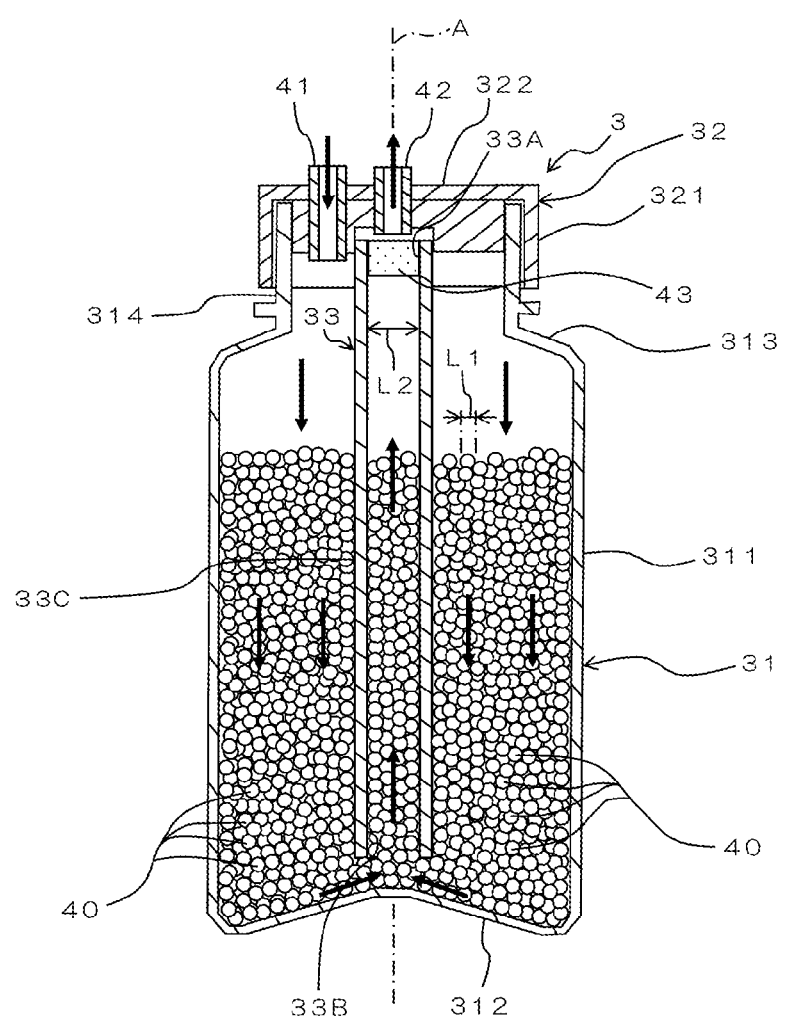
FIG. 2 is a cross-sectional view showing an adsorption apparatus of the chemiluminescence type nitrogen oxide concentration meter of FIG. 1, in which a lid member is attached to a main body.
Figure 3:
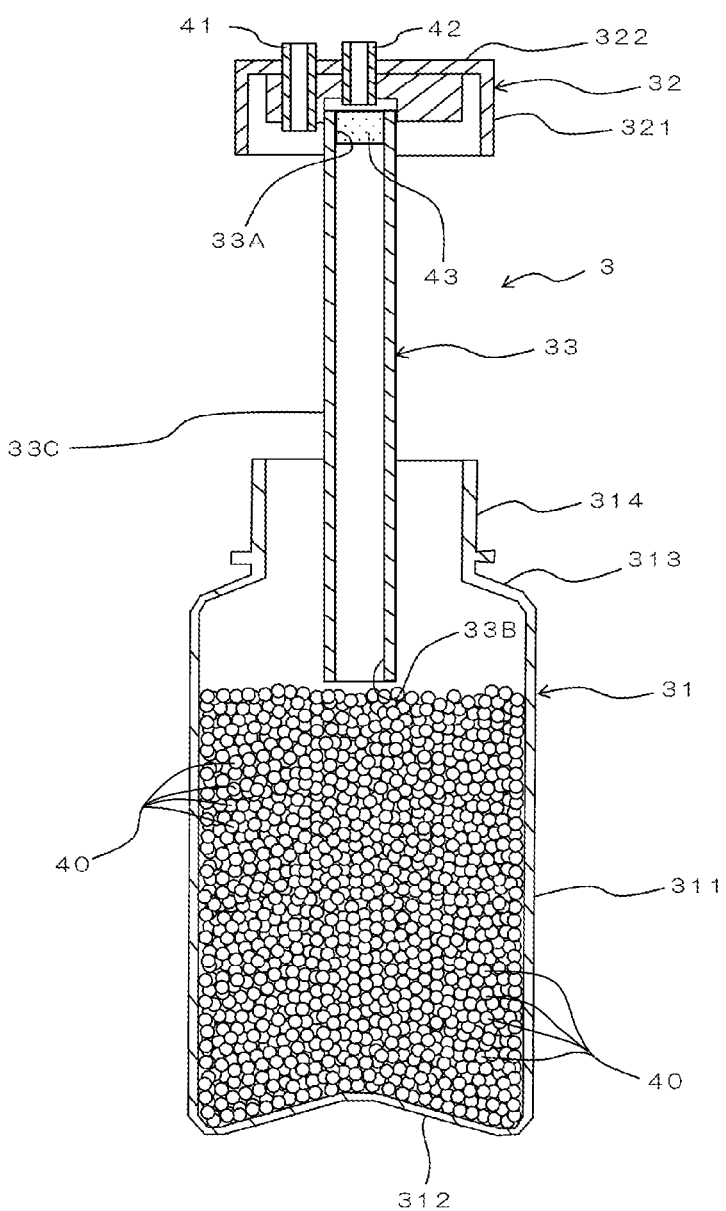
FIG. 3 is a cross-sectional view showing an adsorption apparatus of the chemiluminescence type nitrogen oxide concentration meter of FIG. 1, in which the main body and the lid member are separated.

FIG. 2 is a cross-sectional view showing the adsorption apparatus 3, showing a state where a lid member 32 is attached to a container 31. FIG. 3 is a cross-sectional view showing the adsorption apparatus 3, showing a state where the container 31 and the lid member 32 are separated.

The adsorption apparatus 3 includes the container 31, the lid member 32, and a flow path 33.

The container 31 is formed in a cylindrical shape whose lower end is closed. The container 31 is made of, for example, a resin material, and is formed to be transparent or translucent. The container 31 includes a side surface portion 311, a bottom surface portion 312, a stepped portion 313, and a mounting portion 314.

The side surface portion 311 is formed in a cylindrical shape extending in the vertical direction.

The bottom surface portion 312 is formed in a circular plate shape in plan view and is continuous with the side surface portion 311 so as to close a lower end of the side surface portion 311. The bottom surface portion 312 is formed in a tapered shape directed upward toward the center.

The stepped portion 313 is formed in an annular shape in plan view and continuously protrudes from an upper end of the side surface portion 311 so as to direct radially inward of the side surface portion 311 and upward.

The mounting portion 314 is formed in a cylindrical shape extending in the vertical direction and extends upward from an upper end of the stepped portion 313. A screw thread (not shown) is formed on an outer peripheral surface of the mounting portion 314.

An adsorbent 40 is stored in the container 31 configured as described above. The adsorbent 40 is, for example, silica gel and is made of a plurality of particles. A particle diameter L1 of the adsorbent 40 is, for example, 3.0 to 4.0 mm.

The lid member 32 is a member for sealing the container 31. The lid member 32 includes a side surface portion 321 and an upper surface portion 322.

The side surface portion 321 is formed in a cylindrical shape extending in the vertical direction. A screw groove (not shown) is formed on an inner peripheral surface of the side surface portion 321.

The upper surface portion 322 is formed in a circular shape in plan view and is continuous with the side surface portion 321 so as to close an upper end of the side surface portion 321. An inflow pipe 41 and an outflow pipe 42 are attached to the upper surface portion 322.

The inflow pipe 41 is attached to the upper surface portion 322 so as to penetrate a slightly outer side of the central portion of the upper surface portion 322, and extends in the vertical direction.

The outflow pipe 42 is attached to the upper surface portion 322 so as to penetrate the central portion of the upper surface portion 322, and extends in the vertical direction.

The lid member 32 configured as described above is attached to and detached from the container 31 by being rotated around a rotation axis A extending in the vertical direction.

The flow path 33 is attached to the lid member 32. Specifically, the flow path 33 is attached to the central portion of the bottom surface of the upper surface portion 322 of the lid member 32. The flow path 33 is formed in a cylindrical shape extending in the vertical direction, and the center of the upper surface portion 322 is located on an extension line of the axis. That is, the flow path 33 extends in a straight line along the rotation axis A of the lid member 32. The flow path 33 having an inner portion through which gas passes.

The vertical dimension of the flow path 33 is slightly smaller than the vertical dimension of the container 31. An inner diameter L2 of the flow path 33 is, for example, 1.0 to 2.0 cm. That is, the inner diameter of the flow path 33 is larger than the particle diameter of the adsorbent 40.

An internal space of the flow path 33 communicates with an internal space of the outflow pipe 42 via the upper surface portion 322 of the lid member 32. An internal space at an upper end of the flow path 33 is formed as a vent hole 33A and an internal space at a lower end of the flow path 33 is formed as an opening 33B. Specifically, the flow path 33 has a tip with an opening 33B formed thereon. In the flow path 33, a filter 43 is provided.

The filter 43 is provided in the internal space of the flow path 33 so as to cover the vent hole 33A of the flow path 33.

3. Attachment of Lid Member to Container

When preparing the adsorption apparatus 3, a user first fills the container 31 with the adsorbent 40 in a state where the container 31 and the lid member 32 are separated as shown in FIG. 3. At this time, the adsorbent 40 is filled up to the vicinity of an upper portion of the side surface portion 311 of the container 31. Then, the user disposes the lid member 32 (the lid member 32 and the flow path 33) above the container 31 in this state, and further moves the lid member 32 downward. As a result, the flow path 33 is inserted into the container 31, as shown in FIG. 2.

As described above, the inner diameter L2 of the opening 33B of the flow path 33 is formed larger than the particle diameter L1 of the adsorbent 40. Therefore, the flow path 33 is inserted into the container 31 and the adsorbent 40 enters the flow path 33 via the opening 33B. The portion of the flow path 33 filled with the adsorbent 40 is the filling portion 33C. That is, the filling portion 33C is the central portion and the lower portion of the flow path 33.

Thereafter, the user rotates the lid member 32 around the rotation axis A in a state where the inner peripheral surface of the side surface portion 321 of the lid member 32 is in contact with the outer peripheral surface of the mounting portion 314 of the container 31. As a result, the side surface portion 321 of the lid member 32 and the mounting portion 314 of the container 31 are screwed together, and the lid member 32 is mounted on the container 31.

As described above, the flow path 33 extends in a straight line along the rotation axis A of the lid member 32. Therefore, even when the lid member 32 is rotated, the flow path 33 is arranged in a fixed position along the rotation axis A in the container 31 without moving in the horizontal direction.

In a state where the lid member 32 is mounted on the container 31, the lower end portion (opening 33B) of the flow path 33 is disposed slightly above the central portion of the bottom surface portion 312.

After preparing the adsorption apparatus 3 in this manner, the user connects one end of the middle of the first flow path 21 to the inflow pipe 41, and connects the other end of the middle of the first flow path 21 to the outflow pipe 42, so that the adsorption apparatus 3 is interposed in the first flow path 21.

4. Air Flow in Adsorption Apparatus

Air is flown from the inflow pipe 41 into the adsorption apparatus 3 prepared as described above and interposed in the first flow path 21. The air flowing in from the inflow pipe 41 uniformly moves in a region between the flow path 33 and the container 31 from an upper side to a lower side.

Then, the air comes into contact with the bottom surface portion 312 and is guided to the lower end (opening 33B) of the flow path 33 so as to follow the bottom surface portion 312.

Thereafter, the air flows into the flow path 33 from the opening 33B, and uniformly moves in the flow path 33 from a lower side to an upper side.

As described above, the region between the flow path 33 and the container 31 and the inside of the flow path 33 are filled with the adsorbent 40. Therefore, when the air passes through them, the moisture contained in the air is adsorbed by the adsorbent 40 to be dehumidified.

The dehumidified air passes through the filter 43 provided inside the flow path 33, then flows out from the vent hole 33A, and is returned to the first flow path 21 via the outflow pipe 42. At this time, when foreign matter is contained in the air, the foreign matter is captured and removed by the filter 43.

In this way, when moisture is adsorbed by the adsorbent 40 to be dehumidified, the adsorbent 40 gradually changes its color according to the amount of moisture to be adsorbed. As described above, since the side surface portion 311 of the container 31 is formed to be transparent or translucent, the user visually recognizes discoloration of the adsorbent 40 from the outside of the adsorption apparatus 3 without detaching the lid member 32 from the container 31, and can confirm the replacement time.

5. Action Effect (1) In the present embodiment, as shown in FIG. 2, in the adsorption apparatus 3, the inner diameter L2 of the opening 33B of the flow path 33 is larger than the particle diameter L1 of the adsorbent 40. Therefore, in a state where the flow path 33 is disposed in the container 31, the adsorbent 40 enters the flow path 33 via the opening 33B of the flow path 33. That is, in the adsorption apparatus 3, the adsorbent 40 is disposed in the region between the container 31 and the flow path 33 and inside the flow path 33. Further, in the adsorption apparatus 3, the air flows the region between the container 31 and the flow path 33 and in the flow path 33.

Therefore, when the air is flown into the adsorption apparatus 3, the air can be sufficiently brought into contact with the adsorbent 40, and moisture contained in the air can be sufficiently adsorbed.

(2) Also, in the present embodiment, as shown in FIG. 2, in the adsorption apparatus 3, the filling portion 33C is formed in the flow path 33. The filling portion 33C is filled with an adsorbent 40 in the container 31 which enters from the opening 33B.

Therefore, when the air is flown into the adsorption apparatus 3, the air can be sufficiently brought into contact with the adsorbent 40 in the filling portion 33C.

(3) Moreover, in the present embodiment, as shown in FIG. 2, in the adsorption apparatus 3, the flow path 33 is attached to the upper surface portion 322 of the lid member 32.

Therefore, the operation of inserting the flow path 33 into the container 31 and sealing the container 31 with the lid member 32 can be performed by a series of operations.

As a result, the user's operation can be simplified.

(4) Further, in the present embodiment, as shown in FIG. 2, the flow path 33 extends in a straight line along the rotational axis A of the lid member 32.

Therefore, even when the lid member 32 is rotated with respect to the container 31, the flow path 33 can be arranged in a fixed position along the rotation axis A in the container 31 without moving in the horizontal direction.

As a result, it is possible to prevent the flow path 33 from hindering an attaching/detaching operation of the lid member 32.

Therefore, the lid member 32 can be smoothly attached to and detached from the container 31.

(5) In addition, in the present embodiment, as shown in FIG. 2, the flow path 33 has an end on an opposite side of the opening 33B with a vent hole 33A formed thereon. The air flowing into the adsorption apparatus 3 flows the region between the container 31 and the flow path 33, then flows into the flow path 33 via the opening 33B, further flows in the flow path 33, and then flows out from the flow path 33 via the vent hole 33A.

Therefore, the air can be evenly flown in the container 31. As a result, the air can be sufficiently brought into contact with the adsorbent 40, and the moisture contained in the air can be sufficiently adsorbed by the adsorbent 40.

(6) Moreover, in the present embodiment, as shown in FIG. 2, in the adsorption apparatus 3, the filter 43 is provided in the flow path 33. Then, foreign matter in the air passing through the flow path 33 is captured by the filter 43.

Therefore, it is possible to prevent air mixed with foreign matter from being discharged from the adsorption apparatus 3.

(7) Furthermore, in the present embodiment, as shown in FIG. 1, in the chemiluminescence type nitrogen oxide concentration meter 1, the ozone generator 7 generates ozone using air from which moisture has been adsorbed by the adsorption apparatus 3.

Therefore, it is possible to generate ozone satisfactorily in the ozone generator 7.

In addition, in the chemiluminescence type nitrogen oxide concentration meter 1, chemiluminescence of nitrogen oxides in the sample gas is caused using the ozone satisfactorily generated in the ozone generator 7. The detector 9 detects the intensity of light generated by chemiluminescence in the reaction unit 8. The control unit 10 measures the concentration of nitrogen oxides in the sample gas, based on the intensity of light detected by the detector 9.

Therefore, the concentration of nitrogen oxides in the sample gas can be accurately measured.

6. Modified Examples

In the embodiment described above, the adsorption apparatus 3 has been described as an apparatus for removing moisture contained in the air. However, the adsorption apparatus 3 may be used as an apparatus for adsorbing odor components and soils contained in gas.

Also, in the embodiment described above, the adsorption apparatus 3 has been described as being used for the chemiluminescence type nitrogen oxide concentration meter 1. However, the adsorption apparatus 3 can also be used for apparatus other than the chemiluminescence type nitrogen oxide concentration meter 1.

Further, in the embodiment described above, the adsorbent 40 has been described as being silica gel in the adsorption apparatus 3. However, the adsorbent 40 may be particles made of other materials such as a molecular sieve.

What is claimed is:

1. An adsorption system comprising:
   adsorbent particles that adsorb a component contained in a gas;
   a container containing the adsorbent particles;
   a channel defining a flow path which is inserted into the container, the channel having a distal tip with an opening formed thereon, the opening having a size which is larger than a particle diameter of the adsorbent particles; and
   a pump configured to induce a flow of gas from the container into the opening and through the channel along a length of the channel,
   wherein the container includes a tapered bottom surface portion that is formed to approach the opening towards a center of the container, and
   a portion of the adsorbent particles are located within the distal tip of the channel and extend into the channel a length that is more than half the length of the channel,
   wherein the channel is configured such that gas passing through the channel passes through the opening.

2. The adsorption system according to claim 1, further comprising a lid member for sealing the container, wherein the channel is attached to the lid member.

3. The adsorption system according to claim 2,
   wherein the lid member is attachable to and detachable from the container by being rotated, and
   the channel extends in a straight line along a rotation axis of the lid member.

4. The adsorption system according to claim 2,
   wherein the channel has a vent hole formed on an end of the channel adjacent to the lid member.

5. The adsorption system according to claim 4, further comprising a filter provided inside the channel and configured to capture foreign matter in the gas passing through the channel.

6. The adsorption system according to claim 1, wherein the adsorbent particles are filled up to an upper portion of a side surface portion of the container.

7. A chemiluminescence type nitrogen oxide concentration meter comprising: the adsorption system according to claim 1;
   an ozone generator configured to generate ozone using air from which moisture has been adsorbed by the adsorption system;
   a reactor configured to cause chemiluminescence of nitrogen oxides in a sample gas using ozone generated in the ozone generator;
   a light detector configured to detect an intensity of light generated by chemiluminescence in the reactor; and
   a processor configured to determine a concentration of nitrogen oxides in the sample gas, based on the intensity of light detected by the light detector.

* * * * *